(12) United States Patent
Henningsen et al.

(10) Patent No.: US 7,105,662 B2
(45) Date of Patent: Sep. 12, 2006

(54) METHOD OF PRODUCING N-SUBSTITUTED 2,6-DIALKYLMORPHOLINES

(75) Inventors: Michael Henningsen, Frankenthal (DE); Andreas Kusche, Kleinfischlingen (DE); Michael Hüllmann, Bensheim (DE); Lothar Rüb, Speyer (DE); Stefan Käshammer, Schifferstadt (DE); Till Gerlach, Ludwigshafen (DE)

(73) Assignee: BASF Akteingesellschaft, Ludwigshafen (DE)

( * ) Notice: Subject to any disclaimer, the term of this patent is extended or adjusted under 35 U.S.C. 154(b) by 371 days.

(21) Appl. No.: 10/471,550

(22) PCT Filed: Mar. 15, 2002

(86) PCT No.: PCT/EP02/02916

§ 371 (c)(1),
(2), (4) Date: Sep. 11, 2003

(87) PCT Pub. No.: WO02/074755

PCT Pub. Date: Sep. 26, 2002

(65) Prior Publication Data

US 2004/0077857 A1 Apr. 22, 2004

(30) Foreign Application Priority Data

Mar. 16, 2001 (DE) ................... 101 12 686

(51) Int. Cl.
*C07D 265/30* (2006.01)
(52) U.S. Cl. ..................... 544/165; 544/178
(58) Field of Classification Search ............... 544/165, 544/178
See application file for complete search history.

(56) References Cited

U.S. PATENT DOCUMENTS

| | | | |
|---|---|---|---|
| 2,779,789 A | 1/1957 | Rosenwald et al. | |
| 4,068,077 A | 1/1978 | Goetz et al. | |
| 4,283,534 A * | 8/1981 | Goetz et al. ................ | 544/174 |
| 5,071,851 A | 12/1991 | Buschmann et al. | |

FOREIGN PATENT DOCUMENTS

| | | | |
|---|---|---|---|
| DE | 28 30 999 | * | 1/1980 |
| EP | 111 928 | | 6/1984 |
| GB | 1396 986 | | 7/1975 |
| GB | 1591 144 | | 6/1981 |

OTHER PUBLICATIONS

Koenig et al., Angewandte Chemie 77(1965) S. 327-33.
Derwent Abst, DW 99-71485 = DE 197 20 475.
Derwent Abst, 85-864 = GB 1,591,144.
XP-002292679, 4159-4164.
XP-002202680, 598-693.

* cited by examiner

Primary Examiner—Johann Richter
Assistant Examiner—Ebenezer Sackey
(74) Attorney, Agent, or Firm—Novak Druce & Quigg, LLP

(57) ABSTRACT

The present invention relates to a process for the preparation of N-substituted 2,6-dialkylmorpholines of the formula I

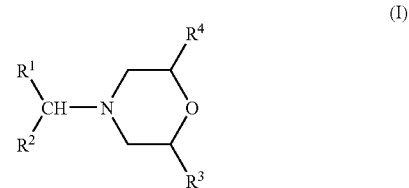

in which $R^1$ and $R^2$, independently of one another, are hydrogen, alkyl or cycloalkyl, or $R^1$ and $R^2$ together with the carbon atom to which they are bonded are a 5- to 14-membered carbocycle, and $R^3$ and $R^4$, independently of one another, are alkyl or cycloalkyl, by reacting at least one carbonyl compound of the formula II

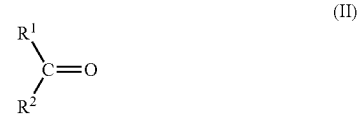

in which $R^1$ and $R^2$ have the meanings given above, with at least one morpholine of the formula III

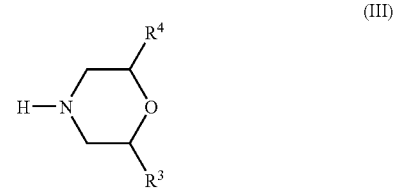

in which $R^3$ and $R^4$ have the meanings given above, in the presence of hydrogen and at least one metal-containing catalyst, wherein the active component of the catalyst consists essentially of platinum group metals.

18 Claims, No Drawings

METHOD OF PRODUCING N-SUBSTITUTED 2,6-DIALKYLMORPHOLINES

The present invention relates to a process for the preparation of N-substituted 2,6-dialkylmorpholines by reacting a carbonyl compound with a secondary amine in a reductive amination.

Tertiary amines form an important class of compounds which is used industrially in extremely diverse sectors. There is therefore a continuous need for the simplest possible processes which permit the preparation of tertiary amines from very readily accessible components in high yields and with high selectivity toward the desired target compound. Among the heterocyclic tertiary amines, the N-substituted tetrahydro-1,4-oxazines (morpholines) are used, for example, in crop protect on.

K. H. König et al. describe, in Angewandte Chemie 77 (1965), pp. 327–333, N-substituted tetrahydro-1,4-oxazines and the use thereof as fungicidal compounds with good action against fungal disorders of cultivated plants. According to this, the preparation of these compounds can, for example, be carried out by dehydrating cyclization of the corresponding bis(2-hydroxyethyl)amines.

DE-A-25 43 279 likewise describes a process for the preparation of N-substituted tetrahydro-1,4-oxazines by single- or two-stage cyclization and hydrogenation of N-substituted bis(2-hydroxyalkyl)amines.

A disadvantage of the process given above is the complex preparation of the starting materials used.

DE-A-197 20 475 describes a process for the preparation of N-alkyl-2,6-dialkylmorpholines in a two-stage synthesis, comprising the preparation of an oxazolidine by reacting corresponding aldehydes or ketones with dialcohols of secondary amines in the presence of an acidic ion exchanger, and the subsequent reaction of the oxazolidine in the presence of hydrogen and a hydrogenation catalyst.

The direct preparation of tertiary amines from carbonyl compounds and specifically from ketones and secondary amines is generally difficult since the target compounds are usually only obtained in low yields, and their isolation is accordingly laborious.

DE-A-33 21 712 describes 2,6-trans-dimethylmorpholine derivatives and the use thereof as fungicides. According to this, the preparation of N-(cyclododecyl)-2,6-dimethylmorpholine (dodemorph), for example, is carried out in a two-stage synthesis, comprising the reaction of cyclododecanone and 2,6-trans-dimethylmorpholine in the presence of p-toluenesulfonic acid to give N-cyclododecenyl-2,6-trans-dimethylmorpholine and the subsequent hydrogenation thereof in the presence of a Pd/C catalyst.

EP-A-0 271 750 describes fungicidal 4-substituted cyclohexylamines. These can be obtained, for example, by reductive amination of cyclohexanones with a secondary amine in the presence of a reducing agent. Suitable reducing agents are hydrogen, formic acid and complex hydrides, such as sodium cyanoborohydride. Suitable catalysts for the reductive amination in the presence of hydrogen are not described. This reaction variant is not demonstrated by a working example either.

DE-A-21 18 283 describes a process for the preparation of secondary or tertiary aliphatic or cycloaliphatic amines by reacting an aliphatic or cycloaliphatic carbonyl compound with ammonia or a primary or secondary amine in the presence of hydrogen and a hydrogenation catalyst, where the catalyst used is a mixture of silver and palladium on a sintered support. A disadvantage of this process is the high costs of the silver catalyst used. In addition, the resulting yields and the selectivities with regard to the target compounds are in need of improvement.

It is an object of the present invention to provide an improved process for the preparation of N-substituted 2,6-dialkylmorpholines. In this connection, the synthesis is to take place starting from carbonyl compounds and secondary amines in a single-stage reaction. Preferably, the process should permit the preparation of tertiary amines in high yields and with high selectivity toward the desired target compounds.

We have now found, surprisingly, that this object is achieved by a process for the preparation of N-substituted 2,6-dialkylmorpholines, in which at least one carbonyl compound is reacted with at least one morpholine derivative in the presence of hydrogen and at least one metal-containing catalyst whose active component consists essentially of platinum group metals, in a reductive amination.

The invention thus provides a process for the preparation of N-substituted 2,6-dialkylmorpholines of the formula I

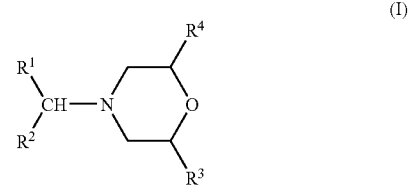

in which $R^1$ and $R^2$, independently of one another, are hydrogen, alkyl or cycloalkyl, or $R^1$ and $R^2$ together with the carbon atom to which they are bonded are a 5- to 14-membered carbocycle, and $R^3$ and $R^4$, independently of one another, are alkyl or cycloalkyl, by reacting at least one carbonyl compound of the formula II

in which $R^1$ and $R^2$ have the meanings given above, with at least one morpholine of the formula III

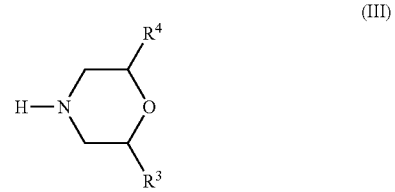

in which $R^3$ and $R^4$ have the meanings given above, in the presence of hydrogen and at least one metal-containing catalyst, wherein the active component of the catalyst consists essentially of platinum group metals.

For the purposes of the present invention, the expression "alkyl" includes straight-chain and branched alkyl groups.

These are preferably straight-chain or branched $C_1$–$C_{20}$-alkyl groups, preferably $C_1$–$C_{12}$-alkyl groups and particularly preferably $C_1$–$C_8$-alkyl groups and very particularly preferably $C_1$–$C_4$-alkyl groups. Examples of alkyl groups are, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, octyl, nonyl, decyl.

Substituted alkyl radicals preferably have 1, 2, 3, 4 or 5, in particular 1, 2 or 3, substituents. These are chosen, for example, from cycloalkyl, aryl, hetaryl, halogen, OH, SH, alkoxy, alkylthio, $NE^1E^2$, $(NE^1E^2E^3)^+$, carboxyl, carboxylate, —$SO_3H$, sulfonate, nitro and cyano.

The cycloalkyl group is preferably a $C_6$–$C_{12}$-cycloalkyl group, such as cyclohexyl, cycloheptyl, cyclooctyl, cyclodecyl or cyclododecyl. Particular preference is given to cyclohexyl and cyclododecyl.

If the cycloalkyl group is substituted, it preferably has 1, 2, 3, 4 or 5, in particular 1, 2 or 3, substituents. These are chosen, for example, from alkyl, alkoxy, alkylthio, OH, SH, cycloalkyl, cycloalkylalkyl, nitro, cyano or halogen.

Aryl is preferably phenyl, tolyl, xylyl, mesityl, naphthyl, anthracenyl, phenanthrenyl, naphthacenyl and, in particular, phenyl or naphthyl.

Substituted aryl radicals preferably have 1, 2, 3, 4 or 5, in particular 1, 2 or 3, substituents. These are chosen, for example, from alkyl, alkoxy, carboxyl, carboxylate, trifluoromethyl, —$SO_3H$, sulfonate, $NE^1E^2$, alkylene-$NE^1E^2$, nitro, cyano or halogen.

Hetaryl is preferably pyrrolyl, pyrazolyl, imidazolyl, indolyl, carbazolyl, pyridyl, quinolinyl, acridinyl, pyridazinyl, pyrimidinyl or pyrazinyl.

Substituted hetaryl radicals preferably have 1, 2 or 3 substituents chosen from alkyl, alkoxy, carboxyl, carboxylate, —$SO_3H$, sulfonate, $NE^1E^2$, alkylene-$NE^1E^2$, trifluoromethyl or halogen.

The above statements regarding alkyl radicals apply correspondingly to alkoxy and alkylthio radicals.

The radicals $NE^1E^2$ are preferably N,N-dimethyl, N,N-diethyl, N,N-dipropyl, N,N-diisopropyl, N,N-di-n-butyl, N,N-di-tert-butyl, N,N-dicyclohexyl or N,N-diphenyl.

Halogen is fluorine, chlorine, bromine and iodine, preferably fluorine, chlorine and bromine.

For the purposes of this invention, carboxylate and sulfonate are preferably a derivative of a carboxylic acid function or of a sulfonic acid function, in particular a metal carboxylate or sulfonate, a carboxylic or sulfonic ester function or a carboxamide or sulfonamide function.

The active component of the catalyst used according to the invention consists essentially of platinum group metals, i.e. Ru, Rh, Pd, Os, Ir, Pt and mixtures thereof.

Preference is given to using a catalyst whose active component is essentially free from silver.

Preference is given to the use of a catalyst whose active component comprises 1 to 100% by weight, preferably 10 to 99% by weight, of Pd, 0 to 60% by weight, preferably 1 to 55% by weight, of Pt, and 0 to 50% by weight, for example 0.1 to 40% by weight, of at least one further metal, which is in particular chosen from Ru, Rh, Os, Ir, Ce, La and mixtures thereof.

In the process according to the invention, preference is given to using a catalyst which comprises a support. Suitable supports are very generally the customary support materials known to the person skilled in the art. These include, for example, carbon-containing support materials, such as activated carbon, silicon carbide, polymeric supports, metal supports, e.g. made of stainless steel, aluminum oxides, silicon dioxides, silicates, alumosilicates, such as zeolites, pumice, diatomaceous earth, silica gel, hydrotalcite, titanium dioxides, zirconium dioxides, zinc oxide, magnesium oxide and combinations and mixtures thereof. Where appropriate, the carrier materials can be doped with alkali metal and/or alkaline earth metal oxides. Particular preference is given to using $\alpha$-$Al_2O_3$, $\gamma$-$Al_2O_3$, $SiO_2$, $TiO_2$, $ZrO_2$ and mixtures thereof. Particular preference is given to $ZrO_2$. The supports can generally have customary forms and can be used, for example, as extrudates (in the form of strands), pellets, beads, tablets, rings, saddles, woven fabric, knits, monoliths, spheres, powders, etc. For a discontinuous process, use as powders is preferred.

The catalysts used can be prepared by generally known processes, for example by impregnation of a support with solutions of compounds or complexes of the metals used. Suitable metal compounds (precursors) are, for example, metal salts, such as nitrates, nitrosyl nitrates, halides, carbonates, carboxylates, metal complexes, such as acetylacetonate, halogen complexes, e.g. chloro complexes, amine complexes etc. The metal compounds can be applied to the support, for example, by common precipitation or impregnation. If two or more metal compounds are used, then these can be applied simultaneously or successively. In this connection, the order in which the active components are applied is usually unimportant. Suitable solvents for the preparation of the catalysts by impregnation are water and organic solvents, such as alcohols, e.g. methanol and ethanol, aromatic compounds, such as benzene and toluene, aliphatic solvents, such as hexane, heptane, etc., cycloaliphatic solvents, such as cyclohexane, etc.

The preparation of supported palladium-containing catalysts is preferably carried out by impregnating a support with a solution of $Pd(NO_3)_2$, $PdCl_2$, $H_2PdCl_4$, Pd acetylacetonate, etc.

Following impregnation, the support is preferably dried. The temperature here is generally in the range from about 50 to 200° C., preferably 100 to 150° C. After drying, the support can be calcined if desired. For this, the temperature is generally in a range from 200 to 600° C., preferably 400 to 500° C. The calcination time can vary within a wide range and is, for example, from about 1 to 10 hours, preferably 1.5 to 5 hours. To convert the precursors into the active component, the catalyst can be treated with a customary reducing agent such as hydrogen. During this treatment, inert gases, such as nitrogen or argon, can be mixed with the reducing agent if desired. The temperatures during the reduction are preferably in a range from about 100 to 500° C., particularly preferably 200 to 300° C. If, for the preparation of the catalysts used according to the invention, a metal compound which is readily thermally decomposable is used as precursor, then these are usually already decomposed to elemental metals or oxidic metal compounds under the calcination conditions, meaning that subsequent reduction is generally not required.

The drying and/or the calcination and/or the reduction can then be followed by at least one further treatment step. These include, for example, passivation, e.g. with oxygen, with which, where appropriate, at least one inert gas can be mixed. The passivation is preferably used for the preparation of catalysts based on metals for which the metal oxides also have catalytic activity.

Further processes for the preparation of catalysts which can be used according to the invention are known to the person skilled in the art and include, for example, vapor deposition, sputtering, ion exchange processes, etc.

According to a suitable embodiment, the catalyst is reduced in situ with hydrogen and thus converted into the active form.

The surface area, the pore volume and the pore size distribution of the catalyst are uncritical within wide ranges.

In the process according to the invention, particular preference is given to using a catalyst which comprises 0.1 to 10% by weight of Pd, based on the weight of active component and support. The catalyst preferably comprises 0 to 5% by weight, such as, for example, 0.1 to 4% by weight, of Pt. Particular preference is given to catalysts which comprise only Pd as active component.

The process according to the invention permits, in an advantageous manner, the single-stage preparation of N-substituted 2,6-dialkylmorpholines. In the process, the target compounds are generally obtained in high yields and with high selectivity. The process according to the invention advantageously permits the preparation of N-substituted 2,6-dialkylmorpholines even in cases of high starting material feed rates, i.e. good space-time yields are generally achieved. A further advantage of the process according to the invention is that the isomerically pure preparation of N-substituted 2,6-dialkylmorpholines is made possible.

Preferably, for the preparation of the N-substituted 2,6-dialkylmorpholines, a ketone of the formula II is used in which $R^1$ and $R^2$ together with the carbon atom to which they are bonded are a 6- to 12-membered carbocycle which may have one, two or three substituents which are chosen, independently of one another, from alkyl, alkoxy, alkylthio, cycloalkyl and cycloalkylalkyl. The compound of the formula II is particularly preferably cyclododecanone.

Preferably, the radicals $R^3$ and $R^4$ in the formula III are, independently of one another, $C_1$–$C_4$-alkyl radicals. Particularly preferably, $R^3$ and $R^4$ are both methyl.

The process according to the invention is particularly suitable for the preparation of N-(cyclododecyl)-2,6-dimethylmorpholine (dodemorph).

The reaction temperature is preferably in a range from 100 to 300° C.

The reaction pressure is preferably 5 to 300 bar, particularly preferably 10 to 250 bar.

The process according to the invention can be carried out without a solvent or in the presence of a solvent. Suitable solvents are water, alcohols, such as methanol and ethanol, ethers, such as methyl tert-butyl ether, cyclic ethers, such as tetrahydrofuran, ketones, such as acetone and methyl ethyl ketone, etc. The morpholine used as starting material is particularly preferably used as solvent. In this connection, the morpholine can be used in an up to 100-fold molar excess relative to the amine component.

The process according to the invention can be carried out batchwise or continuously. Preference is given to the continuous procedure.

Suitable reactors for carrying out the process according to the invention are the customary apparatuses for working under increased pressure known to the person skilled in the art, such as, for example, autoclaves or tubular reactors. The catalyst is preferably used in the form of a fixed bed or another suitable incorporation. The reaction space is preferably arranged vertically.

The reaction preferably takes place on downward flow through the catalyst bed or on upward flow through the catalyst bed. In this connection, the starting materials are preferably introduced such that the entire catalyst layer is essentially continuously covered with liquid.

The invention further provides for the use of a catalyst, as defined above, for the preparation of a tertiary amine by reacting at least one carbonyl compound with at least one secondary amine in the presence of hydrogen.

The invention is described in more detail by reference to the nonlimiting examples below.

EXAMPLES

Example 1 (Comparison Pd/Ag Catalyst)

500 ml of a catalyst which comprised 5% $Ag_2O$ and 0.4% PdO on an $SiO_2$ support were introduced into a vertical tubular reactor. At a temperature of 220° C. and a hydrogen pressure of 100 bar, a mixture, heated to 220° C., of one part of cis-2,6-dimethylmorpholine, one part of trans-2,6-dimethylmorpholine and 0.39 parts of cyclododecanone was pumped in from below at a feed rate of 360 ml/h.

The reaction mixture which emerged comprised, following removal of the 2,6-dimethylmorpholine under reduced pressure, 89.6% of dodemorph and 2.3% of cyclododecanone. This corresponds to a conversion of 97.3% and a selectivity of 91%.

Example 2 (Pd/$ZrO_2$ Catalyst)

The procedure was as in example 1, but using pure cis-2,6-dimethylmorpholine and a Pd/$ZrO_2$ catalyst (palladium content 0.9%). At the same temperature and feed rate and with removal of the 2,6-dimethylmorpholine, the reaction mixture comprised 94.4% of dodemorph and 0.7% of cyclododecanone. This corresponds to a conversion of 99.3% and a selectivity of 95%.

Example 3 (Pd/$ZrO_2$ Catalyst)

The procedure was as in example 2, but with double the feed rate (720 ml/h) and a temperature of 240° C. Following removal of the 2,6-dimethylmorpholine, the reaction mixture comprised 92.2% of dodemorph and 2.6% of cyclododecanone. This corresponds to a conversion of 97.4% and a selectivity of 95%.

Example 4 (Pd/Pt, $ZrO_2$ Catalyst)

The procedure was as in example 1, but using pure cis-2,6-dimethylmorpholine and a Pd/Pt/$ZrO_2$ catalyst (palladium content 0.4%, platinum content 0.4%). At a temperature of 230° C. and a feed rate of 180 ml/h, the reaction mixture comprised, following removal of the 2,6-dimethylmorpholine, 95.6% of cis-dodemorph and no cyclododecanone. This corresponds to a conversion of 100% and a selectivity of 95%.

The invention claimed is:
1. A process for the preparation of N-substituted 2,6-dialkylmorpholines of the formula I

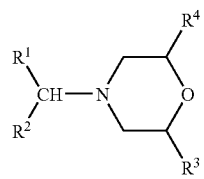 (I)

in which
R$^1$ and R$^2$, independently of one another, are hydrogen, alkyl or cycloalkyl, or R$^1$ and R$^2$ together with the carbon atom to which they are bonded are a 5- to 14-membered carbocycle, and
R$^3$ and R$^4$, independently of one another, are alkyl, or cycloalkyl,
by reacting at least one carbonyl compound of the formula II

 (II)

in which R$^1$ and R$^2$ have the meanings given above, with at least one morpholine of the formula III

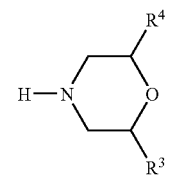 (III)

in which R$^3$ and R$^4$ have the meanings given above, in the presence of hydrogen and at least one metal-containing catalyst, wherein the active component of the catalyst consists essentially of platinum group metals and is essentially free from silver.

2. A process for the preparation of N-substituted 2,6-dialkylmorpholines of the formula I

 (I)

in which
R$^1$ and R$^2$, independently of one another, are hydrogen, alkyl or cycloakyl, or R$^1$ and R$^2$ together with the carbon atom to which they are bonded are a 5- to 14-membered carbocycle, and
R$^3$ and R$^4$, independently of one another, are alkyl or cycloalkyl,
by reacting at least one carbonyl compound of the formula II

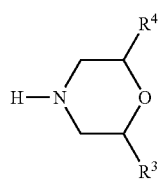 (II)

in which R$^1$ and R$^2$ have the meanings given above, with at least one morpholine of the formula III

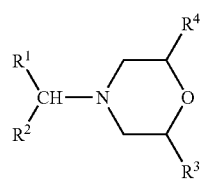 (III)

in which R$^3$ and R$^4$ have the meanings given above, in the presence of hydrogen and at least one metal-containing catalyst, wherein the active component of the catalyst comprises
   1 to 100% by weight of Pd,
   0 to 60% by weight of Pt, and
   0 to 50% by weight of at least one further metal, which is chosen from Ru, Rh, Os, Ir, Ce, La and mixtures thereof.

3. A process as claimed in claim 1, wherein a catalyst is used which comprises a support.

4. A process as claimed in claim 3, wherein the support used is ZrO$_2$.

5. A process as claimed in claim 3, wherein a catalyst is used which comprises 0.1 to 10% by weight of Pd and 0 to 5% by weight of Pt.

6. A process as claimed in claim 1, wherein R$^1$ and R$^2$ together with the carbon atom to which they are bonded are a 6- to 12-membered carbocycle which can have one, two or three substituents which are chosen, independently from one another, from alkyl, alkoxy, alkylthio, cycloalkyl and cycloalkylalkyl.

7. A process as claimed in claim 1, wherein R$^3$ and R$^4$, independently of one another, are C$_1$–C$_4$-alkyl radicals.

8. A process as claimed in claim 1, wherein R$^3$ and R$^4$ are both methyl.

9. A process as claimed in claim 1 wherein the compound of the formula I is N-(cyclododecyl)-2,6-dimethylmorpholine.

10. A process as claimed in claim 4, wherein a catalyst is used which comprises 0.1 to 10% by weight of Pd and 0 to 5% by weight of Pt.

11. A process as claimed in claim 2, wherein a catalyst is used which comprises a support.

12. A process as claimed in claim 11, wherein the support used is ZrO$_2$.

13. A process as claimed in claim 12, wherein a catalyst is used which comprises 0.1 to 10% by weight of Pd and 0 to 5% by weight of Pt.

14. A process as claimed in claim 11, wherein a catalyst is used which comprises 0.1 to 10% by weight of Pd and 0 to 5% by weight of Pt.

15. A process as claimed in claim 2, wherein $R^1$ and $R^2$ together with the carbon atom to which they are bonded are a 6- to 12-membered carbocycle which can have one, two or three substituents which are chosen, independently from one another, from alkyl, alkoxy, alkylthio, cycloalkyl and cycloalkylalkyl.

16. A process as claimed in claim 2, wherein $R^3$ and $R^4$, independently of one another, are $C_1$–$C_4$-alkyl radicals.

17. A process as claimed in claim 2, wherein $R^3$ and $R^4$ are both methyl.

18. A process as claimed in claim 2, wherein the compound of the formula I is N-(cyclododecyl)-2,6-dimethyl-morpholine.

* * * * *